United States Patent
Bakry et al.

(10) Patent No.: US 11,602,491 B1
(45) Date of Patent: Mar. 14, 2023

(54) BIOACTIVE DENTAL TEMPORARY FILLING MATERIAL

(71) Applicant: King Abdulaziz University, Jeddah (SA)

(72) Inventors: Ahmed Samir Ibrahim Bakry, Jeddah (SA); Mona Aly Abbassy, Jeddah (SA); Ali Habiballah Hassan, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/676,279

(22) Filed: Feb. 21, 2022

(51) Int. Cl.
*A61K 6/891* (2020.01)
*A61K 6/62* (2020.01)
*A61K 6/77* (2020.01)
*A61C 5/20* (2017.01)
*A61K 6/74* (2020.01)
*A61K 6/71* (2020.01)
*A61K 6/61* (2020.01)

(52) U.S. Cl.
CPC ........... *A61K 6/891* (2020.01); *A61C 5/20* (2017.02); *A61K 6/61* (2020.01); *A61K 6/62* (2020.01); *A61K 6/71* (2020.01); *A61K 6/74* (2020.01); *A61K 6/77* (2020.01)

(58) Field of Classification Search
CPC ...................................................... A61K 6/836
See application file for complete search history.

(56) References Cited

U.S. PATENT DOCUMENTS

| | | | |
|---|---|---|---|
| 6,313,192 B1 * | 11/2001 | Anstice | C04B 28/00 524/549 |
| 7,090,720 B2 | 8/2006 | Kessler et al. | |
| 9,517,186 B2 | 12/2016 | Rusin et al. | |
| 2014/0193499 A1 | 7/2014 | Da Fonte Ferreira et al. | |
| 2015/0094392 A1 | 4/2015 | Takei et al. | |
| 2017/0274118 A1 * | 9/2017 | Nazhat | A61K 8/24 |
| 2019/0060523 A1 | 2/2019 | Bakry | |
| 2020/0030194 A1 * | 1/2020 | Yoshinaga | A61K 6/62 |

OTHER PUBLICATIONS

Khan et al., "A review of bioceramics-based dental restorative materials", Dental Materials Journal 2019; 38(2): 163-176.

* cited by examiner

*Primary Examiner* — Michael F Pepitone
(74) *Attorney, Agent, or Firm* — WCF IP

(57) ABSTRACT

A dental filling material comprising bioactive borate glass particles, wherein the particles are at a concentration of 40-60 wt %, a co-monomer resin blend, a photoinitiator, and a co-initiator is provided. Method for applying the dental filling material to a tooth structure are also provided. The temporary filling material re-mineralizes the tooth structure and is removed after 1-7 days for the placement of a permanent filling material.

13 Claims, 2 Drawing Sheets

BIOACTIVE DENTAL TEMPORARY FILLING MATERIAL

FIELD OF THE INVENTION

The invention is generally related to a self-adhesive temporary dental filling material containing bioactive borate glass particles in a co-monomer resin blend. The material may be used to fill a cavity after caries removal and serves to re-mineralize the tooth structure until it is removed and a permanent filling material is applied.

BACKGROUND OF THE INVENTION

Dental caries is among the most prevalent diseases in the world (Bakry et al. 2014a). Dental resins and ceramics revolutionized the dental restorative options for patients worldwide by replacing the metallic dental restorations with various types of highly esthetic restorations based on a resinous composite. One of the major advantages of the introduction of resinous composite restorations is its ability to bond to tooth structures with minimum retentive mechanical features of the prepared cavities conducted by the dentist. This unique feature allowed conservation of much of the tooth structure and increased the longevity of teeth in the oral cavities of dental patients. The increased awareness for the importance of conserving as much tooth structure as possible during cavity preparation led to the introduction of the Minimal Intervention Concept (Frencken et al. 2012) that advocated all means to conserve teeth structure and remineralizing any teeth lesions rather than surgically removing all teeth lesions regardless of its depth.

The acceptance of this concept led to change of the caries removal technique done by dentists as only the removal of the caries zones infected by bacteria was advocated, while the zones that are demineralized by bacteria were preserved. However, when applying the resinous restorative materials on demineralized enamel or dentin tissues, the bond strength between them may be jeopardized which may be attributed to increased inter crystalline porosity of the hypomineralized dental tissues, moisture retention within the inter-rods spaces, (William et al. 2006) and higher protein contents (William et al. 2006). So, the idea of remineralizing the demineralized tooth structure proved its efficacy in improving the bond strength between dental tissues and the restorative resin materials (Bakry and Abbassy 2019), but the need of having the remineralizing agents in direct contact with the dental hard tissues for at least 24 hours remained a problem that needs solving. It is a common practice among dentists to place temporary restorations after finishing their cavity preparations for at least 24 hours prior to placing their permanent restorations in next appointment, however, most of the temporary filling materials available in the market do not possess any remineralizing capacity for tooth structure.

The first type of bioactive glasses was introduced by Professor Larry Hench in the 1960s and it was called the 45S5 bioglass (Hench 1991), which had the ability to form a hydroxyapatite rich layer capable of interacting with hard and soft tissues (Hench 1991). Previously, the bioactive glasses were used mainly in the field of orthopedics and periodontology (Hench 1991; Hulbert S. F. 1987; Yamamuro T. 1990). The majority of the literature focused on the use of various compositions of bioactive glasses on bone (Bellucci et al. 2015; Bretcanu et al. 2009; Hu et al. 2009; Sahli et al. 2015) and soft tissues (Mao et al. 2015).

U.S. Pat. No. 10,624,994 (incorporated herein by reference) describes the use of a mixture of borate glass and a phosphoric acid aqueous solution for the re-mineralization of enamel and as a dentin desisitizing agent, however, the aforementioned borate-phosphoric paste physical properties did not enable it to exert a clinically acceptable bonding property to bond composite filling material to enamel and dentin.

SUMMARY

Described herein is a bioactive temporary filling material that can be light cured, thus gaining immediate good mechanical properties, and is able to self-adhere to tooth structures without need for retentive aids.

An aspect of the disclosure provides a dental filling material comprising bioactive borate glass particles, wherein the particles are at a concentration of 40-60 wt %, a co-monomer resin blend, a photoinitiator, and a co-initiator. In some embodiments, a composition of the particles comprises 20-30 mol % $Na_2O$, 20-30 mol % CaO, 1-5 mol % $P_2O_5$, and 40-50 mol % $B_2O_3$. In some embodiments, the resin blend comprises 30-40 wt % bisphenol A diglycidyl ether dimethacrylate (Bis-GMA). In some embodiments, the resin blend further comprises 10-20 wt % ethylene glycol dimethacrylate. In some embodiments, the photoinitiator is 0.05-0.2 wt % camphorquinone. In some embodiments, the co-initiator is 0.05-0.25 wt % ethyl N,N-dimethyl-4-aminobenzoate (EDMAB). In some embodiments, the material does not include phosphoric acid.

Another aspect of the disclosure provides a method for applying a dental filling to a tooth structure, comprising applying a dental filling material as described herein onto an exposed surface of a tooth and curing with light for an effective amount of time to harden the dental filling material. In some embodiments, the method further comprises removing the dental filling material from the tooth and applying a second dental filling material to the tooth. In some embodiments, the removing step is performed 1-7 days after the curing step. In some embodiments, the dental filling material releases calcium and phosphate ions to a hybrid layer when exposed to saliva. In some embodiments, the calcium and phosphate ions form a hydroxyapatite layer on a surface of dentin or enamel to re-mineralize the tooth.

DETAILED DESCRIPTION

Figures 1A, 1B:
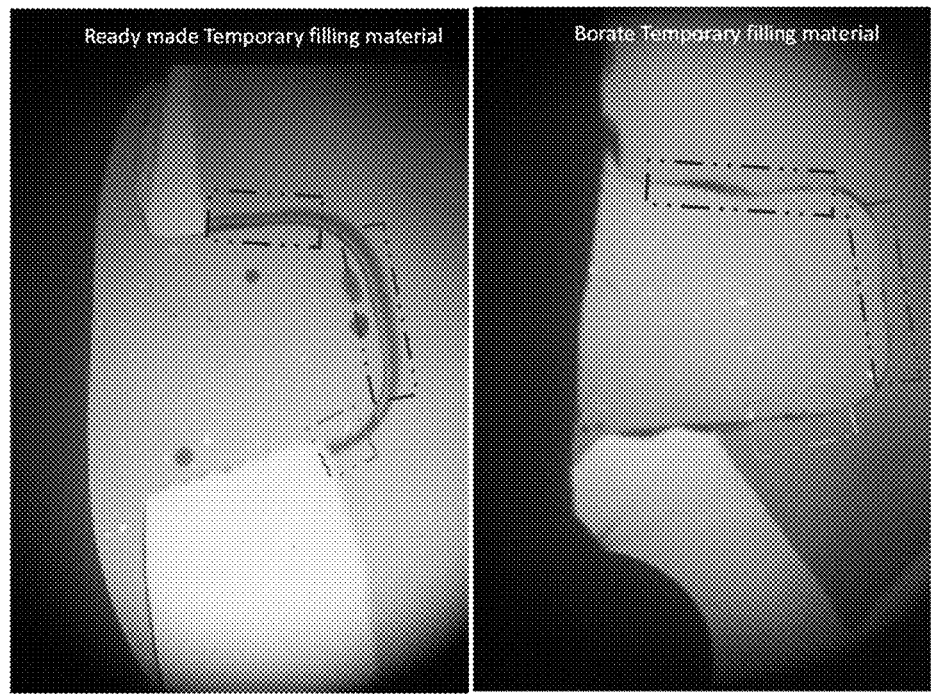
FIGS. 1A-C. Transmicroradiography experimental results. The temporary borate filling material (B) increased the mineral content at the cervical, pulpal and occlusal walls as compared to the ready-made temporary filling material (A). (C) The graph shows that the mineral loss decreased significantly p<0.05 when the borate temporary material was applied.

Embodiments of the disclosure provide bioactive borate glass embedded in a resin blend that is capable of light curing thus obtaining immediate good mechanical properties. This temporary filling material is capable of adhering to tooth structure without need for retentive features. Moreover, this material may act as a potent re-mineralizing agent for demineralized enamel white spot lesions associated with orthodontic treatment or with Molar Incisor Hypomineralization cases.

As used herein, the term "bioactive" refers to a material that generates a positive reaction when in certain biological environments and/or is subjected to a chemical or physical process that modifies the material's surface to form a desired substrate, in this case, for re-mineralization of dentin or enamel. Bioactive materials referred to herein are those with the ability of promoting phosphate mineral (i.e. hydroxyapatite) precipitation when immersed in phosphate-rich physiological medium (i.e. saliva). A bioactive material may also bind chemically with the surrounding bone or promote cell attachment or growth.

The term "glass" refers to a non-crystalline amorphous solid having a breaking stress or surface compressive stress of 10 MPa-30 GPa at 20-40° C. Glass may or may not comprise silica ($SiO_2$).

A "composite" refers to a solid material comprising more than one phase, structure, and/or compound.

In some embodiments, a bioactive borate glass comprises 30-60 mol %, preferably 35-55 mol %, more preferably 40-50 mol % $B_2O_3$ (borate); 10-40 mol %, preferably 15-35 mol %, more preferably 20-30 mol % CaO; 10-40 mol %, preferably 15-35 mol %, more preferably 20-30 mol % $Na_2O$; and 0.5-15 mol %, preferably 1-10 mol %, more preferably 1-5 mol % $P_2O_5$, where each mol % is in mole percents based on 100 mol % of the total composition of the borate bioactive glass which may be generated by a plurality of methods.

In a preferred embodiment, a conventional "melt quench" synthesis method may be used. In this method, the borate bioactive glass may have a Ca:P molar ratio of 1:1-17:1, preferably 2:1-10:1, more preferably 3:1-7:1. The borate bioactive glass may be made by melting glass precursors such as carbonate salts, a phosphate salt, and boric acid ($H_3BO_4$) to form a glass. For example, the glass precursors, $Na_2CO_3$, $CaCO_3$, $H_3BO_4$, $NaH_2PO_4$, as well as others as needed, may be ground into powders using a mortar and pestle, or obtained as powders, and mixed to yield 20-40 g of final glass product. These powders may comprise particles having largest dimensions of 0.1-200 μm, preferably 0.5-100 μm, more preferably 1-50 μm. Preferably the mixed powder contains a ratio of the glass precursors to generate an equivalent mole percent as mentioned above. In other embodiments, different glass precursors may be used to ultimately produce equivalent compositions after melting to form a glass. For instance, $Na_2B_4O_7$ may be used in place of $H_3BO_4$, or $Na_2HPO_4$ may be used in place of $NaH_2PO_4$. A person having ordinary skill in the art may be able to determine a practical amount of glass precursors to form a glass having one of the aforementioned compositions.

Some examples of preparation and treatment steps of borate glass particles are herein incorporated by reference (U.S. Pat. No. 10,624,994 to Bakry). According to some preferred embodiments, the powder mixture of glass precursors may be heated in a furnace, oven, kiln, air, Pt or Pt alloy crucible, then allowed to cool to room temperature and molded, crushed or ground to produce borate bioactive glass in the form of particles. In one embodiment, the powder mixture heated in a Pt crucible was quenched on a stainless-steel plate and pressed with another plate to obtain glass plate pieces with a thickness of 0.2-1 mm. In this embodiment, the glass particles were obtained in a porcelain mortar and further pulverized using agate planetary mill. Alternatively, a sol-gel method may be used to form the borate bioactive glass particles at lower temperatures. In addition, the particles from different glass powders may be mixed and re-melted to form the bioactive glass particles.

In one embodiment, the borate bioactive glass particles may further comprise $Ca(PO_3)_2$, $K_2O$, $TiO_2$, $CaF_2$, $Fe_2O_3$, CuO, SrO, $Bi_2O_3$, $Ce_2O_3$, $Ga_2O_3$, and/or ZnO, preferably $TiO_2$, $CaF_2$, $Fe_2O_3$, CuO, SrO, and/or ZnO, more preferably $TiO_2$, SrO, and/or ZnO. Preferably, these compounds or precursors to these compounds are added to the powder mixture before the heating and melting. It is possible that one or more of $Ca(PO_3)_2$, $K_2O$, $TiO_2$, $CaF_2$, $Fe_2O_3$, CuO, SrO, $Bi_2O_3$, $Ce_2O_3$, $Ga_2O_3$, and/or ZnO may be present in the bioactive borate glass, each at a weight percentage of 0-10 wt %, preferably 0.2-8 wt %, more preferably 0.4-6 wt %, even more preferably 0.5-3 wt %, relative to a total weight of the borate bioactive glass particles.

In a preferred embodiment, the borate glass product may be further treated with 3-6 vol % of g-methacryl-oxypropyl-trimethoxysilane (g-MPS) in acetone with 0.1-0.5 vol % of water in order to cover the exposed hydroxyl groups of the borate glass particles and to coat the hydroxyls with silane-like molecules, thus making the surface chemically inert. In this embodiment, the borate bioactive glass particles are substantially free of $Al_2O_3$, $SiO_2$ or MgO. The term "substantially free of $Al_2O_3$, $SiO_2$ or MgO" refers to the condition in which the $SiO_2$ content, the $Al_2O_3$ content, the MgO content, or all three are less than 0.5 wt %, preferably less than 0.2 wt %, more preferably less than 0.1 wt % with respect to the total weight of the borate bioactive glass. In some embodiments, borate bioactive glass being completely free of Si, Al or Mg may not be possible due to sample impurities or environmental contamination. In an alternative embodiment, the borate bioactive glass particles may comprise particles clustered together as agglomerates.

The borate bioactive glass particles disclosed herein may have overall shapes that are spherical, ellipsoidal, oblong, ovoidal, angular, rectangular, prismoidal, or some other shape. The borate bioactive glass particles may have sharp, acute, pointed, or jagged edges. In one embodiment, the borate bioactive glass particles have longest dimensions or diameters of 1-200 μm, preferably 2-100 μm, more preferably 5-40 μm. Small bioactive glass (i.e. the particles with diameters of 1-5 μm or 1-3 μm) may be used to facilitate mixing and/or to more quickly dissolve in any application solutions known in the art. Further, the present disclosure relates to borate bioactive glass particles that are not in phosphoric acid solution or are free of any other acidic solutions.

In some embodiments, the borate bioactive glass particles may have submicron diameters, such as 100-900 nm, preferably 200-800 nm. As the average diameter of dentinal tubules is about 1 μm, particles with submicron diameters may be able to enter a dentinal tubule. The ratio of the longest dimension to the shortest dimension of the borate bioactive glass particles may be 1:1-1:10, preferably 1:1.05-1:5, more preferably 1:1.1-1:2. In one embodiment, the borate bioactive glass particles have longest dimensions within 75-125% of the average particle longest dimension, preferably within 80-120%. In one embodiment, the borate bioactive particles may have surface area to volume ratios of 15 $nm^{-1}$-50 $\mu m^{-1}$, preferably 0.3 $\mu m^{-1}$-10 $\mu m^{-1}$ more preferably 0.8 $\mu m^{-1}$-5 $\mu m^{-1}$ and bulk densities of 1-8 $g/cm^3$, preferably 1.2-5 $g/cm^3$, more preferably 1.5-4 $g/cm^3$. In some embodiments, the borate bioactive glass particles may have pores with diameters of 1-12 nm, preferably 1.5-8 nm, more preferably 1.8-5 nm, which may provide higher surface area to volume ratios.

To manufacture the borate bioactive glass temporary filling material, a resin blend is added and mixed with the borate bioactive glass particles described above. In one embodiment, the (optionally silanated) borate glass is incorporated with a co-monomeric resin blend at a concentration of, preferably 40-60 wt %, e.g. 45-55 wt %, more preferably about 50 wt %, relative to a total weight of the borate bioactive filling material. In some embodiments, the borate glass does not exceed 50 wt % such that it has low enough physical and mechanical properties to facilitate its removal after a few days of application to the tooth.

In one embodiment, the resin blend comprises 30-40 wt %, e.g. about 34.75 wt %, of bisphenol A diglycidyl ether dimethacrylate (Bis-GMA) or other dimethacrylate monomers, such as, 10-20 wt % of ethylene glycol dimethacrylate. Other examples of non-degradable polymers that may be added to the material include polymethylmethacrylate, polyhydroxyethylmethacrylate (HEMA), urethane dimethacrylate (UDMA), triethylene glycol dimethacrylate (TEGDMA).

The contact surface between the bioactive borate material and the treated tooth are hardened or cured by a plurality of adhering methods (e.g. light-activated or chemical polymerization) and by applying the required method for an effective time to cure and/or form a hydroxyapatite layer on the surface of the dentin or enamel to re-mineralize the tooth. In a preferred embodiment, the effective time of light curing is about 10-40 seconds. The effective time of light curing may be adjusted accordingly based on the volume, material and/or intended purposes of the bioactive system. As used herein, "hardening" or "curing" a composition are used interchangeably and refer to polymerization and/or crosslinking reactions including, for example, photopolymerization reactions and chemical polymerization techniques.

In certain embodiments, the filling material is photopolymerizable, i.e., the hardenable component is photopolymerizable and the hardener includes a photoinitiator (or photoinitiator system), in which irradiation with actinic radiation initiates the polymerization (or hardening) of the material. Some exemplary photoinitiators that may be incorporated into the material include camphorquinone (CQ), 2,4,6-trimethylbenzoyl-diphenylphosphine oxide (TPO), bisacylphosphine oxide (BAPO), benzophenone (BP), 9,10-phenanthrenequinone (PQ), 1-phenyl-1,2 propanedione (PPD), 9-(2,4,6-trimethylbenzoyl)-9-oxytho-9-phosphafuluorene (TMBOPF), 9-(p-toluyl)-9-oxytho-9-phosphafuluorene (TOPF), benzoyltrimethylgermane (BTMGe), dibenzoyldiethylgermane (DBDEGe), ivocerin-dibenzoyl germanium (IVO) and 7-ethoxy-4-methylcouramrin-3-yl) phenyliodo-nium hexafluoroantimonate (P3C-SB). In some embodiments, the photoinitiator is present in an amount of 0.05-0.2 wt %. The most preferred photoinitiator, in this embodiment, is camphorquinone, which can work by itself but becomes more efficient with further incorporation of co-initiators. The most commonly used co-initiators are ethyl-4-(dimethylamino(benzoate (EDMAB), NN-dimethyl-p-toluidine (DMPT), and 2(NN-dimethylamino)ethyl methacrylate (DMAEMA). In some embodiments, the co-initiator is present in an amount of 0.05-0.25 wt %. Alternatively, the compositions of the filling material are chemically polymerizable, i.e., the compositions contain a chemically polymerizable component and a chemical initiator that can polymerize, cure, or otherwise harden the composition without dependence on irradiation with actinic radiation. Such chemically polymerizable compositions are sometimes referred to as "self-cure" compositions and may include glass ionomer cements, resin-modified glass ionomer cements, redox cure systems, and combinations thereof.

Additionally, medicaments or other therapeutic substances can be optionally added to the filling material. Examples include, but are not limited to, fluoride sources such as tertbutyl ammonium tetrafluoroborate, whitening agents, anticaries agents, calcium sources, phosphorus sources, re-mineralizing agents (calcium phosphate compounds), enzymes, breath fresheners, anesthetics, clotting agents, acid neutralizers, chemotherapeutic agents, immune response modifiers, antimicrobial agents, antifungal agents, desensitizers, and the like. Combinations of any of the above additives may also be employed. Furthermore, the filling material, especially at the manufacturing steps of borate bioactive glass particles, may further comprise a salt such as $KNO_3$, $NaF$, $SnF_2$, $SrCl_2$, and/or $CaCl_2$, preferably $NaF$, $SnF_2$, and/or $CaCl_2$, more preferably $NaF$ and/or $SnF_2$. These salts may provide beneficial effects to dentin and enamel re-mineralization; for instance, fluoride from $NaF$ or $SnF_2$ may intercalate and strengthen a hydroxyapatite lattice within or on an enamel or dentin layer. The salt may be present at a weight percentage of 0.1-10 wt %, preferably 0.2-5 wt %, more preferably 0.25-4 wt % relative to a total weight of the borate bioactive glass filling material.

Previously available temporary dental filling materials are inert materials whose only function is to fill the dental cavity prepared by the dentists and prevent the impaction of food in these cavities for a scheduled next appointment with the dentist. During this period (at least 24 hours and may be extended to be 10 days or more), the tooth enamel and dentin surfaces and internal structures do not benefit from the chemical components of the temporary filling material. Moreover, the wide spread of Molar Incisor Hypomineralization syndrome (which involves the presence of white spot demineralization regions on the enamel of molars and incisors in children) without clearly determining the cause or effective treatment of this syndrome is one of the major challenges faced by dentists worldwide. Due to the dynamic nature of the oral cavity, most of the re-mineralizing agents will be dissolved and washed out by the action of saliva. The demineralization of tooth structure and the subsequent caries destruction to the dental tissues leads to the early loss of teeth with subsequent increase of burden on health service organizations worldwide.

The borate temporary filling material described herein has the ability to release calcium and phosphate ions to be applied on enamel and dentin hypomineralized surfaces and adhere to these surfaces for at least 24 hours releasing a high amount of calcium and phosphate to the demineralized enamel and dentin tissues. The temporary filling material enables the transfer of large quantities of calcium and phosphate ions from the temporary filling material to the internal structures of the dental enamel and dentin rendering these surfaces more resistant to caries and more suitable to receive the final resinous restorations. Moreover, the borate temporary filling material can improve the color of the demineralized enamel white spot lesions by re-mineralizing these enamel lesions. The borate glass has excellent adhesive properties that enables it to adhere effectively to the enamel and dentin walls and at the same time attain acceptable mechanical properties due to its light cured matrix. The borate glass temporary filling material, when exposed to the oral saliva, starts slow releasing the borate glass particles in the resin matrix to the surrounding dental hard tissue and starts forming calcium-phosphate compounds on top of the dental enamel and dentin and eventually these compounds will dissolve by the salivary action and penetrate the structure of the enamel and dentin causing their re-mineralization by the calcium and phosphate compounds. The ions released from the borate glass will not be washed out by the action of the saliva but will be in intimate contact with the enamel and dentin surfaces due to the adhesive properties of the temporary filling material. This adhesive property aids the borate temporary filling in releasing all its rich components of calcium and phosphate to the tooth structure causing the improvement of the physical and mechanical properties of tooth structures. The borate glass released calcium and phosphate compounds eventually crystallize to form hydroxyapatite which is the same chemical structure of the dental enamel and dentin and thus a chemical bond may be formed between the hydroxyapatite formed by the borate glass and the biologic hydroxyapatite of the tooth structure.

Embodiments of the disclosure include methods of applying the dental filling to a tooth structure including steps of applying the dental filling material onto an exposed surface of a tooth and curing with light for an effective amount of time to harden the dental filling material. The material may be used to temporarily fill a cavity created after removal of caries. The material is self-adhesive and no additional adhesive material or binder needs to be added to the composition or the surface of the tooth. After 1-20 days, e.g. 1-10 days, e.g. 1-7 days, the temporary filling material is removed and a permanent dental filling material, e.g. a resinous restoration, is applied to the tooth. The permanent filling material can remain in the tooth for several years. The mode of treatment by the borate temporary filling material improves the characteristic of the tooth structures and leads to the resistance of these treated tooth structures to caries and erosive attacks leading to the increased longevity of the teeth.

The borate bioactive glass filling material may be applied to a location of a tooth having an eroded or removed enamel and/or dentin layer, or having an early erosion lesion, which may be caused by chemical erosion, such as exposure to acidic compounds, beverages, or foods, or may be caused by physical abrasion, such as by filing or grinding. In one embodiment, this location to receive the borate bioactive glass filling material may have exposed dentinal tubules. In another embodiment, an enamel and/or dentin layer may be removed by a physical impact against a tooth, which may result in a chipped tooth. Similarly, a physical impact may result in a cracked tooth having a fissure with exposed dentinal tubules. In another embodiment, the location may be within or on a cavity or depression caused by tooth decay (i.e. dental caries). In another embodiment, the location may be located below the gum line or at a place where the gum has receded. Alternatively, the borate bioactive glass filling material may be applied to a surface of a tooth that is not enamel or dentin, for example, the cementum. As non-limiting examples, the tooth may be an incisor, a cuspid, a bicuspid, a premolar, or a molar, and may be a primary tooth or a permanent tooth. The borate bioactive glass filling material may be placed by means of a dental spatula, an elevator, an applicator, or a brush, or may be applied by extruding from a tube or syringe. In one embodiment, where the borate bioactive glass filling material is applied by an applicator, it may be applied by a Microbrush applicator. In one embodiment, the borate bioactive glass filling material may be applied to fill a cavity or depression on the surface of the tooth, so that the borate bioactive glass filling material lies flush against the surface of the tooth. In other embodiments, an amount of borate glass filling material may be applied that is less than that required for a flush surface (thus leaving a concave surface or a surface within the tooth), or the amount of borate bioactive glass filling material may be greater than that required for a flush surface (thus leaving a convex shape). The ratio of the applied volume of the borate bioactive glass filling material to the volume of the tooth above the gum line may be 1:200-1:1, preferably 1:50-1:2, more preferably 1:40-1:5. In an alternative embodiment, a single volume of borate bioactive glass filling material may not be placed just on a single tooth, but on two or more teeth as a contiguous volume, such as filling a gap between two teeth.

The bioactive borate glass filling material may potentially be used for non-dental bone structures as well. Since bones can often regenerate, materials for bone repair should be selected based on their abilities in slow degradation to components that may be used for tissue renewal and/or safe removal afterward.

Since dentin is covered in a hard outer layer of calcium phosphate mineral containing enamel, which is the hardest substance in the human body, when the enamel is cracked, chipped, or decayed, the dentin is exposed to acid and bacteria build up. While bones are mostly made of collagen, dentin is composed of 45% of mineral hydroxyapatite, 33% of organic material and 22% of water. The bioactive borate glass composition can further provide a method of treating dentin hypersensitivity comprising applying at least one surface of a tooth sample having at least one indication of dentin hypersensitivity with a formulation including any of the disclosed compositions.

In one embodiment, before applying the borate bioactive filling material, the surface of the tooth may be cleaned or prepared by air jet, water jet, polishing, brushing, drilling, scraping, grinding, acid etching, or de-mineralizing. Acid etching or de-mineralizing may be done with a solution comprising citric acid, phosphoric acid, EDTA, hydrochloric acid, acetic acid, or some other inorganic acid, organic acid, or chelating agent. In one embodiment, preparation of the surface by drilling, scraping, grinding, acid etching, or de-mineralizing may increase the surface roughness and provide additional crevices for a layer of calcium phosphate to deposit and anchor. The surface roughness on the prepared tooth, for example, within a 10 μm×10 μm region, may possess an Ra roughness value of 0.10-0.30 μm, preferably 0.12-0.25 μm. However, in some embodiments, a tooth may already have an equivalent surface roughness by erosion and may not need additional abrasion or etching.

For storage, the borate bioactive glass filling material may be formed in advance and then stored for 1-12 months, preferably 2-8 months, more preferably 3-6 months in an airtight container and stored at room temperature, or in a refrigerator or freezer. In another embodiment, a mixture of the borate bioactive glass particles, resin blend, photoinitiator and co-initiator may be formed in advance and stored. In another embodiment, each component may be prepared separately and, within 20 minutes or 10 minutes of application to a tooth, the mixture may be made to form the borate bioactive glass filling material.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example

Materials and Methods
Method of Manufacturing the Borate Glass

Borate-based bioactive glass with the composition of 24.4 $Na_2O$-26.9 CaO-2.6 $P_2O_5$-46.1 $B_2O_3$ in mol % was prepared by a conventional melt-quenching method. The reagent grade $Na_2CO_3$, $CaCO_3$, $H_3BO_4$ and $NaH_2PO_4$ $2H_2O$ were mixed as the glass yield of 30 g by using an aluminum mortar. The resulting mixture was put in a Pt crucible and then heated in an electric furnace in air for 1 h at 1450° C. The melt was quenched by pouring it on a stainless steel plate and pressed with another plate to obtain glass plate pieces with the thickness of 0.2-1 mm Glass particles were obtained by crushing the glass using a porcelain mortar and pestle. The glasses were pulverized (less than 90 micron) using agate planetary mill and were treated with g-methacryloxypropyltrimethoxysilane (g-MPS) (Aldrich Chemical Co., Milwaukee, Wis.) in acetone.

Synthesis of Borate Temporary Filling Material

The Borate glass was incorporated at a concentration of (50 wt %) into a co-monomers resin blend (DA) consisting of 34.75 wt % bisphenol A diglycidyl ether dimethacrylate (Bis-GMA), 15% Ethylene glycol dimethacrylate, 0.15 wt % ethyl N,N-dimethyl-4-aminobenzoate (EDMAB) (Co-initiator), and 0.1 wt % camphorquinone (CQ) (Initiator). The whole mixture was placed in opaque bottles and placed in ultrasonic bath for two minutes.

Transmicroradiography Experiment

Class V cavities were prepared on the buccal and lingual surfaces of 20 lower freshly extracted third molars. The occlusal margins of the prepared cavities were in enamel and the gingival margins located at the cemento-enamel junction. Using a cylindrical marked diamond point the cavity preparation was performed so that the dimensions were standardized, (4.0 mm in width, 3.0 mm in height, and 2 mm in depth). The buccal cavities received the ready-made temporary fillings while the lingual cavities received the borate temporary filling.

Simulated Caries Acidic Challenge

All teeth having the class V cavities had their surfaces masked with two layers of nail varnish leaving the cavity cavo-surface margins and cavity walls uncovered by the nail varnish. The uncovered tooth structures were challenged with buffered demineralization solution (2.2 mM $CaCl_2$), 10 mM $NaH_2PO_4$, 50 mM acetic acid, 100 mM NaCl, 1 ppm NaF, 5 mM $NaN_3$; pH 4.5).

Borate Glass Temporary Glass Application

The buccal cavities' demineralized walls received the ready-made temporary material while the lingual cavities received the light curing borate temporary filling followed by light curing for 30 seconds. The specimens were stored in a remineralizing solution of 1.5 mM $CaCl_2$), 0.9 mM $NaH_2PO_4$, 0.13M KCl and 5 mM $NaN_3$ adjusted to pH 7.0 with HEPES buffer for 24 hours. The cavities were completely washed out by distilled water followed by thorough drying.

Transmicroradiography Analysis

The teeth were split vertically with an Isomet® diamond saw (Isomet® 5000; Buehler, Lake Bluff, Ill.) into buccal and lingual cavities. The cavities were dehydrated in ascending alcohol solutions), immersed in styrene monomer (2 h), and embedded in polyester resin (Rigolac, Oken, Tokyo, Japan). The cavities were filled with flowable composite and light cured for 30 seconds. The specimens were cut into sections approximately 130 to 150 µm in thickness using a low-speed diamond saw (Isomet® 5000; Buehler, Lake Bluff, Ill.) and then ground to obtain sample thicknesses ranging between 100-120 microns. TMR images were taken for the slices using an x-ray generator (CMR 2; Softex, Tokyo, Japan) at 25 kV voltage and 4 mA current for 20 min, with a Ni filter). The distance between the x-ray tube and the specimen was 15 cm. The TMR images, together with 15 aluminum step-wedges (each 15 µm in thickness), were captured in the x-ray glass plate film (High Precision Photo Plate PXHW, Konica Minolta Photo, Tokyo, Japan) and scanned as 8-bit digital images using a CCD camera (DP70, Olympus, Tokyo, Japan) attached to a microscope (BX41, Olympus). Mean mineral profiles (mineral density versus depth) were created using software. The gray values obtained after digitizing the TMR images were converted to number of the aluminum step wedges by special equations (brightness vs. number of the step wedge), and the relative mineral density (%) was calculated as number of the step wedge in the sound (non-demineralized) area being 100%. Then the relative % was converted to vol % as the 100% in the sound area being 87 vol % [7,27,28]. The lesion depth (LD, μm) was defined as a distance from the lesion surface where the mineral density was 5% less than that in the sound area. The mineral loss ($\Delta Z$, vol. % μm) was determined by the integrated mineral loss from the lesion surface to the lesion depth [21].

Spectrophotometer Experiment Results 10 anterior teeth that were freshly extracted had their surfaces masked by nail varnish leaving a treatment window of 6 mm width and 3 mm length. The created demineralized enamel region was measured by a spectrophotometer (Ray-Plicker, Limoge, France.). The Borate temporary filling material was applied onto the demineralized area once every week for 4 weeks. The specimens during the application period were stored in remineralizing solution 1.5 mM $CaCl_2$, 0.9 mM $NaH_2PO_4$, 0.13M KCl and 5 mM $NaN_3$ adjusted to pH 7.0 with HEPES buffer. After the end of the re-mineralization period (30 days), the same tooth was examined again by the spectrophotometer.

Results

Figure 1C:
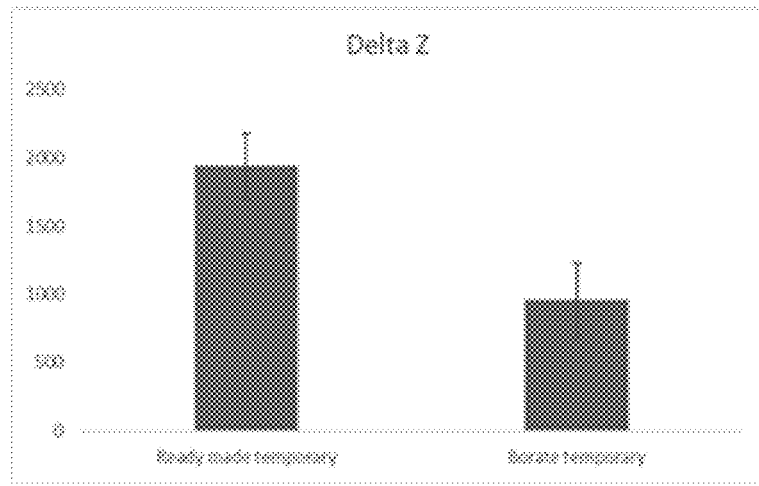

The transmicroradiography experimental results are shown in FIGS. 1A-C. The temporary borate filling material increased the mineral content at the cervical, pulpal and occlusal walls as compared to the ready-made temporary filling material (FIG. 1A-B). Mineral loss decreased significantly $p<0.05$ when the borate temporary material was applied (FIG. 1C).

The spectrophotometer results (not shown) demonstrated that application of the borate temporary material once per week for four weeks improve the shade of an enamel demineralized white spot lesion from a shade of 2R15 (Vita 3D shade) to 4M1.

Figure 2A:
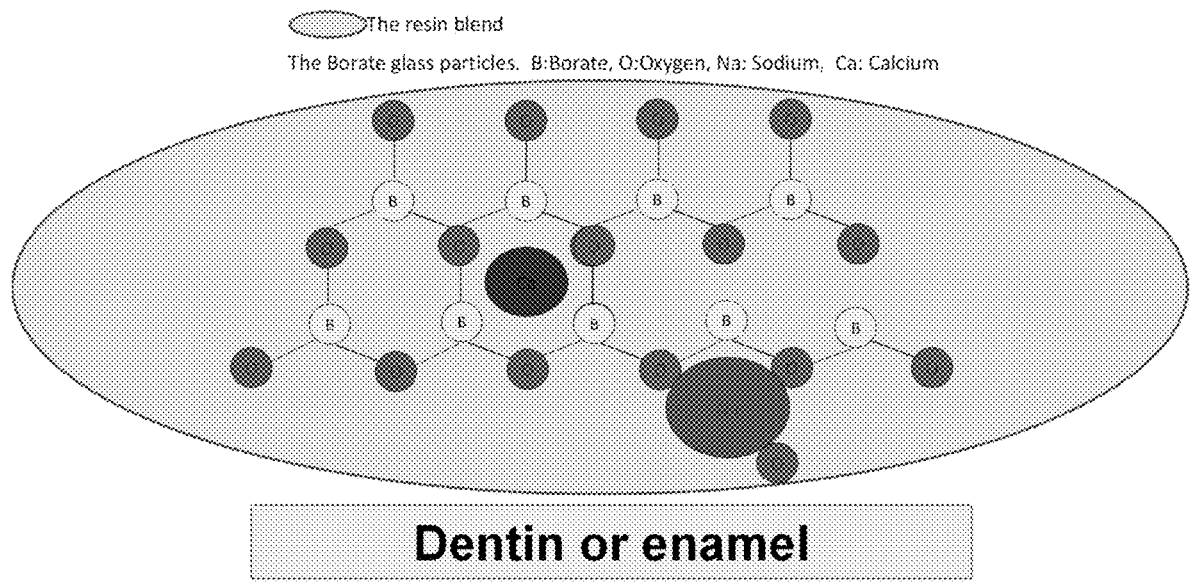
FIGS. 2A-B. Mechanism of the borate glass bonding treatment for dentin or enamel. (A) The borate glass particles embedded in the resin blend are applied to a dentin or enamel surface. (B) Calcium and phosphate ions released from the borate particles re-mineralize the dentin or enamel structures.
Figure 2B:
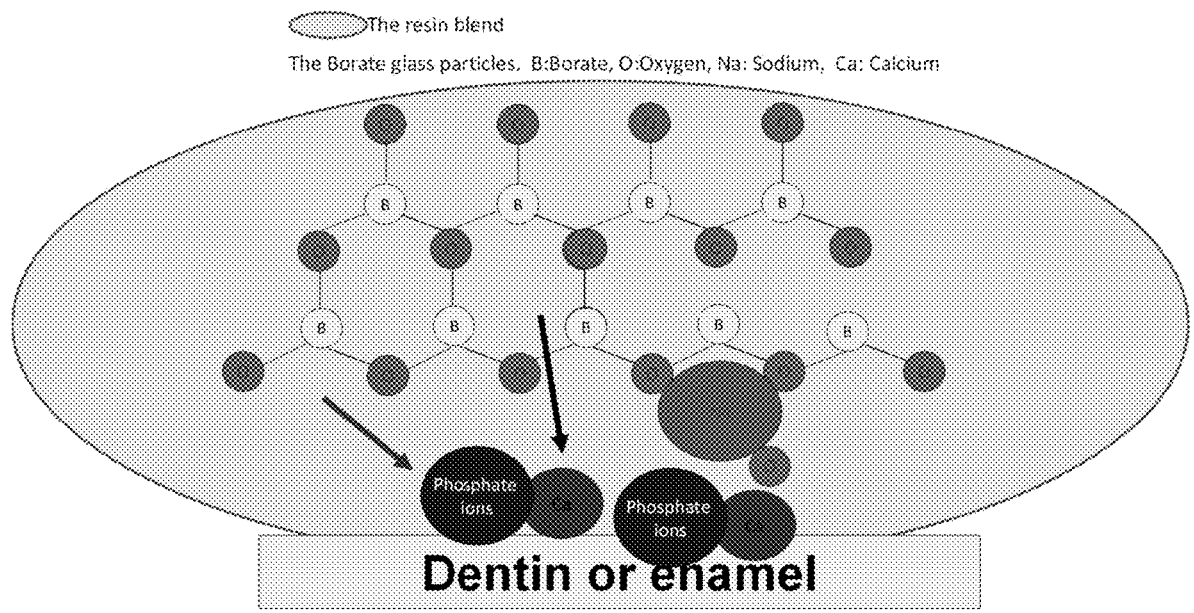

FIGS. 2A-B show a mechanism of the borate glass bonding treatment for dentin or enamel. The borate glass particles embedded in the resin blend are applied to a dentin or enamel surface (FIG. 2A). Calcium and phosphate ions are then released from the borate particles and re-mineralize the dentin or enamel structures (FIG. 2B).

CONCLUSION

The borate temporary filling material has the ability to adhere to enamel and dentin hypomineralized surfaces for at least 24 hours releasing a high amount of calcium and phosphate to the demineralized enamel and dentin tissues. Previously available temporary dental filling materials are inert materials whose only function is to fill the dental cavity prepared by the dentists and prevent the impaction of food in these cavities for a scheduled next appointment with the dentist. During this period (at least 24 hours and may be extended to be 10 days or more), the tooth enamel, dentin surfaces, and internal structures do not benefit from the chemical components of the temporary filling material. The presently disclosed borate temporary filling material enables the transfer of large quantities of calcium and phosphate ions from the temporary filling material to the internal structures of the enamel and dentin rendering these surfaces more resistant to caries and more suitable to receive the final resinous restorations.

The borate temporary filling material can also improve the color of the demineralized enamel white spot lesions by remineralizing these enamel lesions. Previously available remineralizing materials in the market do not have this capability.

Acknowledgement

This project was funded by Science and Technology Unit-King Abdulaziz University-Kingdom of Saudi Arabia-award number UE-41-101.

REFERENCES

Bakry A S, Abbassy M A. 2019. The efficacy of a bioglass (45s5) paste temporary filling used to re-mineralize enamel surfaces prior to bonding procedures. J Dent. 85:33-38.

Bakry A S, Marghalani H Y, Amin O A, Tagami J. 2014a. The effect of a bioglass paste on enamel exposed to erosive challenge. J Dent. 42(11):1458-1463.

Bakry A S, Takahashi H, Otsuki M, Sadr A, Yamashita K, Tagami J. 2011a. Co2 laser improves 45s5 bioglass interaction with dentin. Journal of dental research. 90(2):246-250.

Bakry A S, Takahashi H, Otsuki M, Tagami J. 2014b. Evaluation of new treatment for incipient enamel demineralization using 45s5 bioglass. Dental materials: official publication of the Academy of Dental Materials. 30(3): 314-320.

Bakry A S, Tamura Y, Otsuki M, Kasugai S, Ohya K, Tagami J. 2011b. Cytotoxicity of 45s5 bioglass paste used for dentine hypersensitivity treatment. Journal of dentistry. 39(9):599-603.

Bellucci D, Sola A, Anesi A, Salvatori R, Chiarini L, Cannillo V. 2015. Bioactive glass/hydroxyapatite composites: Mechanical properties and biological evaluation. Mater Sci Eng C Mater Biol Appl. 51:196-205.

Bretcanu O, Misra S, Roy I, Renghini C, Fiori F, Boccaccini A R, Salih V. 2009. In vitro biocompatibility of 45s5 bioglass-derived glass-ceramic scaffolds coated with poly (3-hydroxybutyrate). J Tissue Eng Regen Med. 3(2):139-148.

Frencken J E, Peters M C, Manton D J, Leal S C, Gordan V V, Eden E. 2012. Minimal intervention dentistry for managing dental caries—a review: Report of a fdi task group. Int Dent J. 62(5):223-243. Hench L L. 1991. Bioceramics—from concept to clinic. Journal of the American Ceramic Society. 74(7):1487-1510.

Hu S, Chang J, Liu M, Ning C. 2009. Study on antibacterial effect of 45s5 bioglass. J Mater Sci Mater Med. 20(1): 281-286.

Hulbert S. F. BJC, Hench L. L., Wilson J., Heimke G. 1987. Ceramics in clinical applications: Past, present, and future. Amesterdam, Netherlands: Elsevier.

Mao C, Chen X, Miao G, Lin C. 2015. Angiogenesis stimulated by novel nanoscale bioactive glasses. Biomed Mater. 10(2):025005.

Stahli C, James-Bhasin M, Hoppe A, Boccaccini A R, Nazhat S N. 2015. Effect of ion release from cu-doped 45s5 bioglass(r) on 3d endothelial cell morphogenesis. Acta Biomater. 19:15-22.

William V, Burrow M F, Palamara J E, Messer L B. 2006. Microshear bond strength of resin composite to teeth affected by molar hypomineralization using 2 adhesive systems. Pediatr Dent. 28(3):233-241.

Yamamuro T. HLL, Wilson J. 1990. Handbook of bioactive ceramics, vol ii: Calcium phosphate and hydroxyl apatite ceramics. Boca Raton, Fla.: CRS Press.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A dental filling material comprising:
bioactive borate glass particles, wherein the particles are at a concentration of 40-50 wt %;
a co-monomer resin blend, wherein the bioactive borate glass particles are embedded in the co-monomer resin blend;
a photoinitiator; and
a co-initiator,
wherein the material does not include phosphoric acid.

2. The dental filling material of claim 1, wherein a composition of the particles comprises 20-30 mol % $Na_2O$, 20-30 mol % CaO, 1-5 mol % $P_2O_5$, and 40-50 mol % $B_2O_3$.

3. The dental filling material of claim 1, wherein the resin blend comprises 30-40 wt % bisphenol A diglycidyl ether dimethacrylate (Bis-GMA).

4. The dental filling material of claim 3, wherein the resin blend further comprises 10-20 wt % ethylene glycol dimethacrylate.

5. The dental filling material of claim 1, wherein the dental filling material comprises 0.05-0.2 wt % camphorquinone as the photoinitiator.

6. The dental filling material of claim 1, wherein the dental filling material comprises 0.05-0.25 wt % ethyl N,N-dimethyl-4-aminobenzoate (EDMAB) as the co-initiator.

7. The dental filling material of claim 1, wherein the bioactive borate glass particles are prepared using a melt quench synthesis method.

8. A dental filling material comprising:
bioactive borate glass particles, wherein the particles are at a concentration of 40-50 wt % and wherein a composition of the particles comprises 20-30 mol % $Na_2O$, 20-30 mol % CaO, 1-5 mol % $P_2O_5$, and 40-50 mol % $B_2O_3$;
a co-monomer resin blend, wherein the bioactive borate glass particles are embedded in the co-monomer resin blend and wherein the resin blend comprises 30-40 wt % bisphenol A diglycidyl ether dimethacrylate (Bis-GMA);
0.05-0.2 wt % camphorquinone as a photoinitiator; and
0.05-0.25 wt % ethyl N,N-dimethyl-4-aminobenzoate (EDMAB) as a co-initiator, wherein the material does not include phosphoric acid.

9. A method for applying a dental filling to a tooth structure, comprising:
applying the dental filling material of claim 8 onto an exposed surface of a tooth; and
curing with light for an effective amount of time to harden the dental filling material.

10. The method of claim 9, further comprising:
removing the dental filling material from the tooth; and
applying a second dental filling material to the tooth.

11. The method of claim 10, wherein the removing step is performed 1-7 days after the curing step.

12. The method of claim 9, wherein the dental filling material releases calcium and phosphate ions to a hybrid layer when exposed to saliva.

13. The method of claim 12, wherein the calcium and phosphate ions form a hydroxyapatite layer on a surface of dentin or enamel to re-mineralize the tooth.

* * * * *